US011369452B2

(12) United States Patent
Bacher et al.

(10) Patent No.: US 11,369,452 B2
(45) Date of Patent: Jun. 28, 2022

(54) WIDE-ANGLE ENDOILLUMINATOR

(71) Applicant: Alcon Inc., Fribourg (CH)

(72) Inventors: Gerald David Bacher, Carlsbad, CA (US); Omeed Paydar, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/151,777

(22) Filed: Jan. 19, 2021

(65) Prior Publication Data

US 2021/0220077 A1 Jul. 22, 2021

Related U.S. Application Data

(60) Provisional application No. 62/963,739, filed on Jan. 21, 2020.

(51) Int. Cl.
*A61B 90/30* (2016.01)
*A61B 1/06* (2006.01)
*A61B 1/07* (2006.01)

(52) U.S. Cl.
CPC ............ *A61B 90/30* (2016.02); *A61B 1/0623* (2013.01); *A61B 1/07* (2013.01); *A61B 2090/306* (2016.02)

(58) Field of Classification Search
CPC . A61B 90/30; A61B 2090/306; A61B 1/0623; A61B 1/0661; A61B 1/07; A61B 1/00096; A61B 1/06; A61B 1/0684
See application file for complete search history.

(56) References Cited

U.S. PATENT DOCUMENTS

| | | | |
|---|---|---|---|
| 7,618,177 B2 | 11/2009 | Cazzini | |
| 7,731,710 B2 | 6/2010 | Smith | |
| 7,837,372 B2 | 11/2010 | Hickingbotham | |
| 8,012,146 B2 | 9/2011 | Hickingbotham | |
| 8,480,279 B2 | 7/2013 | Papac et al. | |
| 8,485,972 B2 | 7/2013 | Papac et al. | |
| 8,968,347 B2 | 3/2015 | McCollam | |
| 9,066,678 B2 | 6/2015 | Auld | |
| 9,072,587 B2 | 7/2015 | Smith | |
| 9,364,982 B2 | 6/2016 | Schaller | |
| 9,402,643 B2 | 8/2016 | Auld | |
| 9,956,053 B2 | 5/2018 | Diao | |
| 10,016,248 B2 | 7/2018 | Mirsepassi | |
| 10,295,718 B2 | 5/2019 | Mirsepassi | |
| 10,869,735 B2 | 12/2020 | Diao et al. | |
| 10,952,808 B2 | 3/2021 | Johnson | |
| 2006/0184162 A1 | 8/2006 | Smith | |
| 2006/0245702 A1* | 11/2006 | Cazzini | A61B 3/0008 385/115 |

(Continued)

OTHER PUBLICATIONS

Alcon Retina Catalog, V4, pp. 15-31, Copyright 2019.

*Primary Examiner* — Eduardo C Robert
*Assistant Examiner* — Christina Negrellirodriguez

(57) ABSTRACT

Certain embodiments describe an endoilluminator comprising a probe housing an optical fiber. The probe comprises a distal end with an opening through which a first light from a distal end of the optical fiber is configured to be propagated. The probe comprises one or more side openings through which a second light from one or more sides of the optical fiber is configured to be propagated. The endoilluminator also comprises a handpiece coupled to a light source and the proximal end of the probe, wherein the light source is configured to drive light into the optical fiber.

15 Claims, 5 Drawing Sheets

(56) References Cited

U.S. PATENT DOCUMENTS

2008/0177257 A1    7/2008  Smith et al.
2014/0121469 A1    5/2014  Meckel et al.
2020/0390598 A1   12/2020  Charles

* cited by examiner

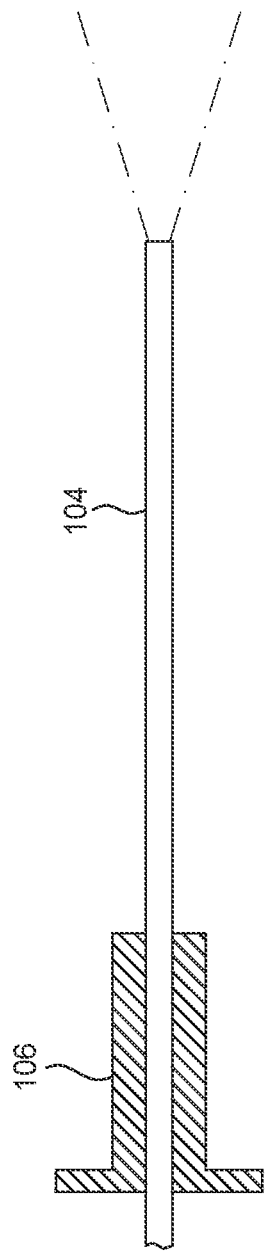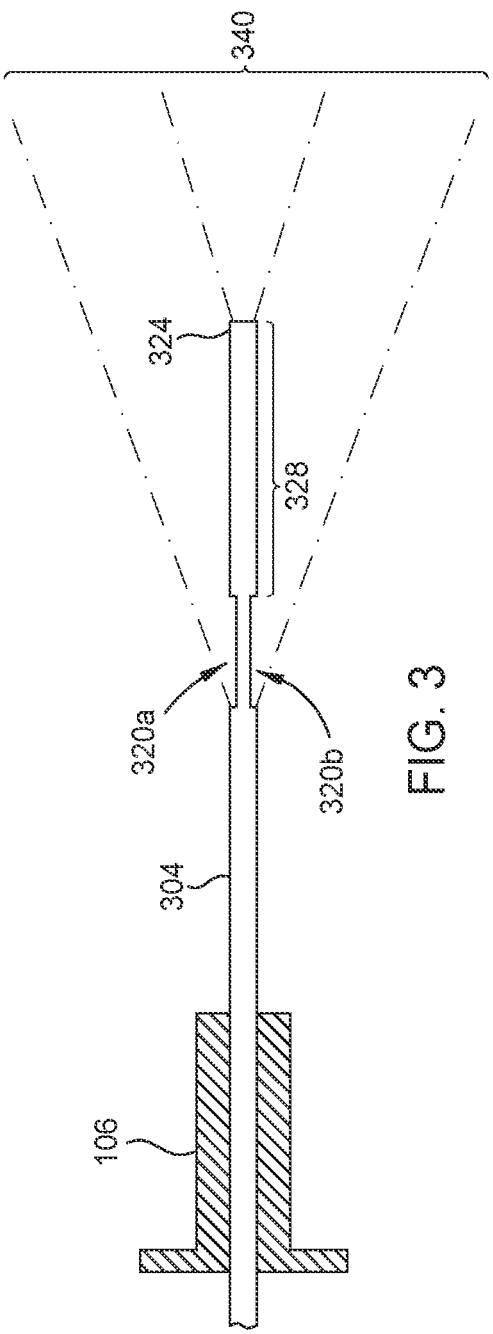

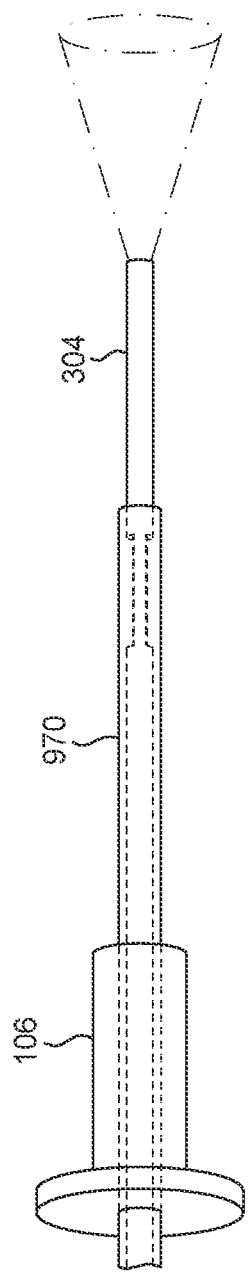
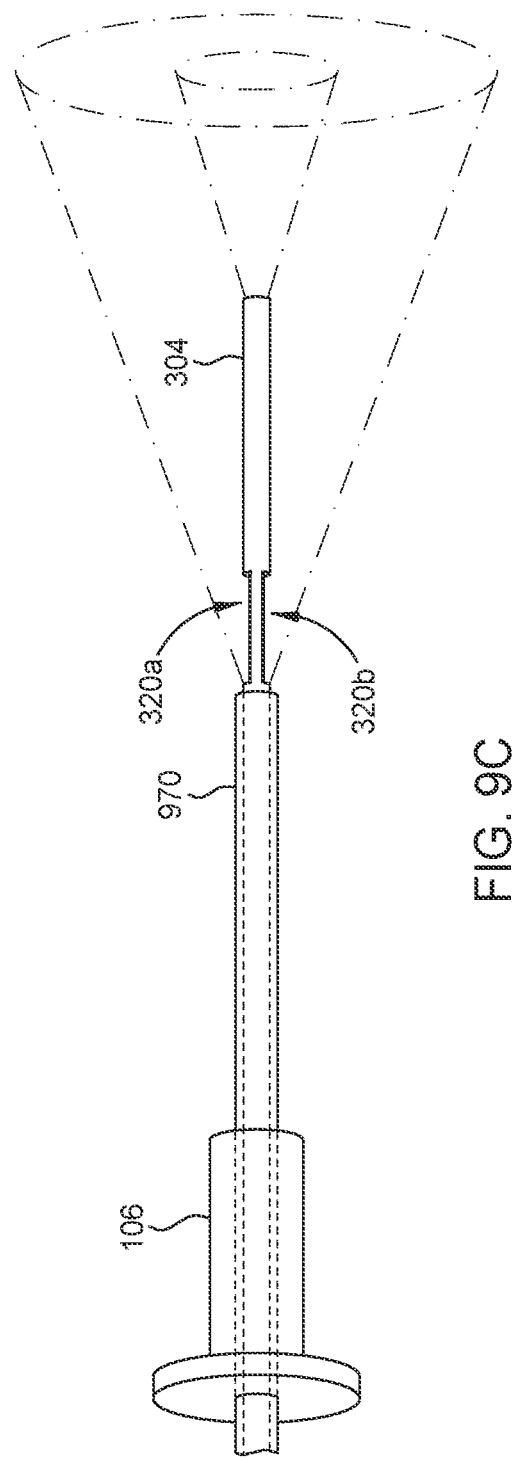

WIDE-ANGLE ENDOILLUMINATOR

PRIORITY CLAIM

This application claims the benefit of priority of U.S. Provisional Patent Application Ser. No. 62/963,739 titled "WIDE-ANGLE ENDOILLUMINATOR," filed on Jan. 21, 2020, whose inventors are Gerald David Bacher and Omeed Paydar, which is hereby incorporated by reference in its entirety as though fully and completely set forth herein.

TECHNICAL FIELD

This application relates to ophthalmic endoilluminators and more particularly to a wide-angle endoilluminator for ophthalmic surgery.

BACKGROUND

Ophthalmic illuminators allow a surgeon to illuminate the interior of an eye such as the vitreous and the retina during surgical procedures. For example, an ophthalmic illuminator (endoilluminator) includes a handpiece coupled to a shaft or probe configured to be inserted into the eye through an insertion cannula. In some cases, the endoilluminator includes a fiber optic element within a bore of the probe. By driving a proximal end of the fiber optic element with a suitable light source, light emitted from a distal end of the fiber illuminates a desired portion of the eye during a surgical procedure. A user (e.g., an ophthalmic surgeon) may illuminate the vitreous chamber of the eye with the endoilluminator while using an ophthalmic microscope or a digital visualization system (e.g., Alcon NGENUITY® "heads-up surgery" visualization system) to observe the eye when performing surgical maneuvers.

BRIEF SUMMARY

The present disclosure relates generally to ophthalmic endoilluminators and more particularly to a wide-angle endoilluminator for ophthalmic surgery.

Certain aspects provide an endoilluminator comprising a probe housing an optical fiber. The probe comprises a distal end with an opening through which a first light from a distal end of the optical fiber is configured to be propagated. The probe comprises one or more side openings through which a second light from one or more sides of the optical fiber is configured to be propagated. The endoilluminator also comprises a handpiece coupled to a light source and the proximal end of the probe, wherein the light source is configured to drive light into the optical fiber.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 2 illustrates a partial view of the probe of the endoilluminator of FIG. 1, according to some embodiments of the present disclosure.

FIG. 3 illustrates an example of a probe with two side openings, according to some embodiments of the present disclosure.

FIGS. 9A-9C illustrate an example sleeve or outer tube that surrounds the probe of FIG. 3, according to some embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present disclosure may be discussed relative to certain embodiments and figures below, all embodiments of the present disclosure can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

As used herein, the term "proximal" refers to a location with respect to a device or portion of the device that, during normal use, is closest to the console that the device is coupled to and farthest from the patient in connection with whom the device is used. Conversely, the term "distal" refers to a location with respect to the device or portion of the device that, during normal use, is farthest from the console and closest to the patient in connection with whom the device is used. For example, the terms "distal" and "proximal" as used herein may refer to a relative location with respect to an endoilluminator.

Figure 1:
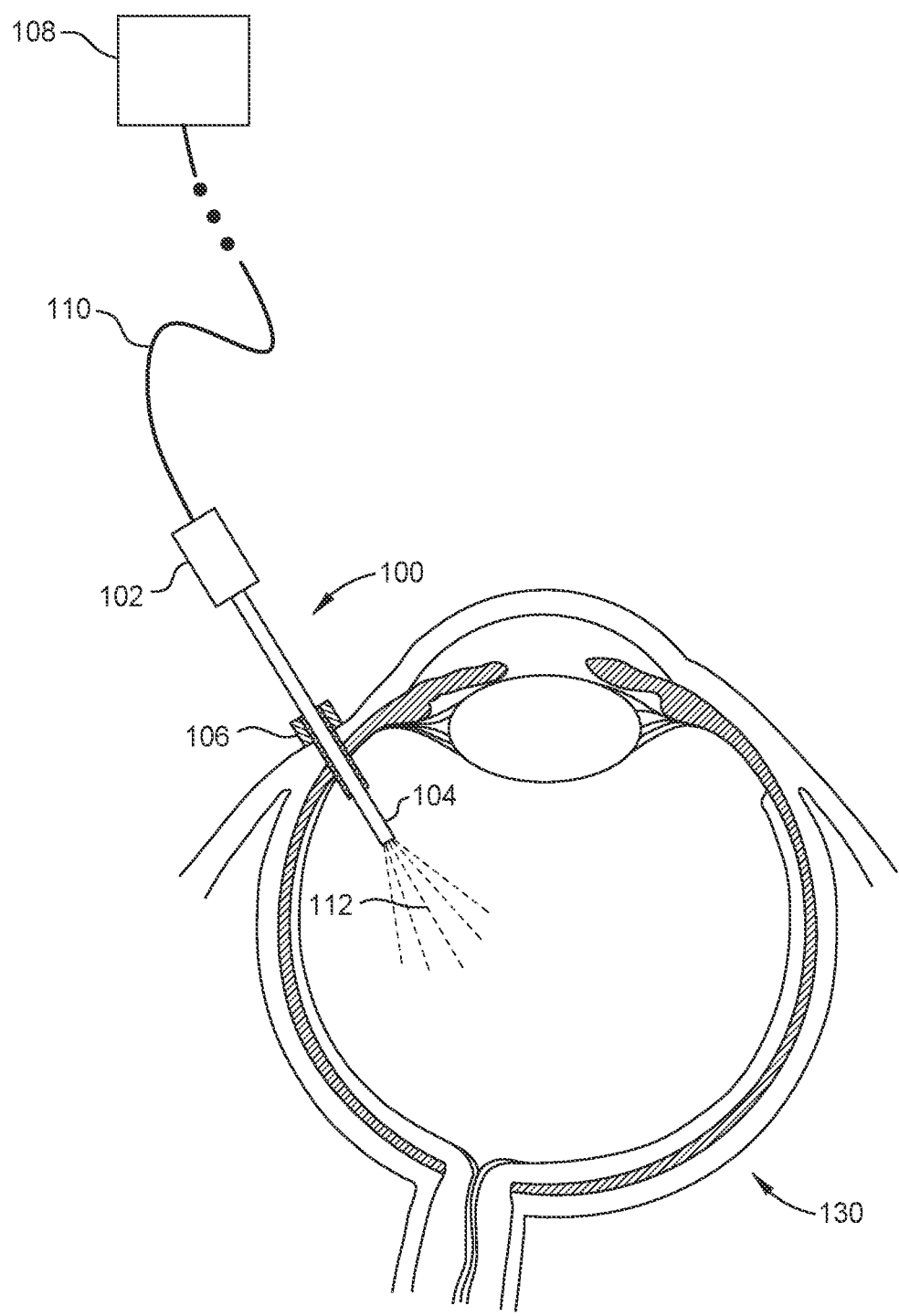
FIG. 1 illustrates a side view of a conventional endoilluminator emitting light onto a retinal region of an eye.

FIG. 1 illustrates a cross-sectional view of an eye 130 having an endoilluminator 100 inserted therein to provide a source of light in the eye globe. The endoilluminator 100 includes a handpiece 102 coupled to (e.g., fixedly) the proximal end of a probe 104. The handpiece 102 is configured to provide a user (e.g., an ophthalmic surgeon) with a graspable portion of the endoilluminator 100 to provide the surgeon a means for manipulating the depth and location of the probe 104 within the eye 130, and for directing the emitted light 112. Probe 104, which may also be referred to as a probe tip, is a substantially hollow shaft (e.g., made out of stainless steel) or hypodermic tubing, configured to be inserted into the eye 130 via an insertion cannula 106. Although the probe 104 of FIG. 1 is illustrated as a straight shaft, other embodiments include a probe 104 having other shapes. For example, a portion of the probe 104 may be curved to provide light to regions of the eye that would be difficult to illuminate with a straight probe 104.

The endoilluminator 100 is further configured to house an optical fiber configured to direct light out of a distal end of the probe 104. In particular, the hollow portion of the probe 104 includes an interior compartment configured to house the optical fiber. The optical fiber may include one or more cores. The distal end of the probe 104 comprises an opening (i.e., distal end opening) through which the distal end of the optical fiber is able to propagate illumination light on to the eye.

Handpiece 102 is removably coupled to a distal end of a fiber optic cable 110 having a proximal end coupled to a light source 108. Fiber optic cable 110 comprises a jacket (e.g., a Polyvinyl chloride (PVC) jacket) that surrounds a portion of the optical fiber that does not extend through endoilluminator 100. The light source 108 drives light into the entry-point of the proximal end of the optical fiber within fiber optic cable 110. It should be noted that in some embodiments, light source 108 is not external to the handpiece 102. For example, in certain embodiments, the handpiece 102 contains light source 108 within a housing or structure of the handpiece 102.

FIG. 2 illustrates a partial view of probe 104 of the endoilluminator 100 of FIG. 1, which is inserted through an insertion cannula 106. As shown, light is emitted only from the distal end of probe 104. However, in certain cases, the surgeon may benefit from a larger or wider-angle beam of light.

Accordingly, certain embodiments described herein are directed to providing a wide-angle endoilluminator with a probe having one or more openings through which the optical fiber within the probe is able to emit light from the sides of the probe and, thereby, provide a larger beam of light to the surgeon.

FIG. 3 illustrates an example of a probe 304 with two side openings ("openings") 320a and 320b (collectively referred to as openings 320) provided at a distance 328 from the distal end 324 of probe 304. Openings 320 are in the form of slots or slits (e.g., rectangular slots) on the sides of probe 304. Openings 320 may be created by, for example, cutting pieces (e.g., rectangular pieces) out of a probe, such as probe 104. Openings 320 expose the optical fiber within probe 304, thereby, allowing the optical fiber to emit light through openings 320. FIG. 3 illustrates an example of the beam of light created with a diameter 340 that is larger than the diameter of the beam emitted from the distal end 324 of probe 304. The beam emitted from the distal end 324 of probe 304 (i.e., opening of distal end 324), is provided by the distal end of the optical fiber that is housed by probe 304. In some embodiments, the distal end 324 of probe 304 is flush with the distal end of the optical fiber.

Note that in some of the embodiments described and shown herein, including the embodiment of FIG. 3, two openings 320 are provided. However, in some other embodiments, there may be a fewer or a larger number of openings on probe 304. For example, in some embodiments, there is only one opening. Also, in some other embodiments, instead of two openings, three or more openings may be placed at the same distance 328 from the distal end 324. In such an example, there are three or more slots around probe 304, where all the openings have the same distance 328 from the distal end 324, and where each of the openings is narrower than each of the openings 320.

In the embodiment of FIG. 3, openings 320 are provided such that they both have the same distance 328 from the distal end 324 of probe 304. The distance 328 is measured from the distal end of the openings 320 to the distal end 324. However, in some other embodiments, each opening may be provided at a different distance, measured from the distal end 324. Also, in some embodiments, openings 320 may be placed at a location with a distance from the distal end 324 that is smaller or greater than distance 328. In one example, openings 320 may be provided at the distal end 324 of probe 304, such that, for example, the distance between the openings in that case and the distal end 324 would be equal to zero. Changing the location of openings 320 along probe 304 may impact the width of the beam of light that is propagated into the eye globe.

Also, in some embodiments, multiple openings may be provided at a first distance from the distal end 324 and multiple other openings may be provided at a second distance from the distal end 324. For example, in the example of FIG. 3, in addition to openings 320, two or more openings (e.g., similar to openings 320) may be provided at a location with a distance from the distal end 324 that is greater or smaller than distance 328.

Further, in some of the embodiments described and shown herein, including the embodiment of FIG. 3, openings 320 are in the form of slots. However, in other embodiments, openings may be in any form, shape, or length. Some examples include circular, ellipse-shaped, or square-shaped openings. Also, in some embodiments, a combination of different shapes or forms of openings may be provided. In certain embodiments, openings 320 may have a larger length. Providing openings, similar to openings 320, but with larger lengths may allow for emitting a beam with a larger width. In one example, openings 320 may extend all the way to the distal end 324 of probe 304.

Figure 4:
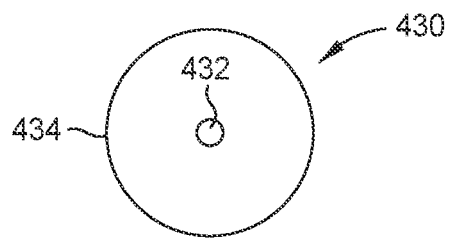
FIG. 4 illustrates an example front view of an optical fiber with a core and a cladding, according to some embodiments of the present disclosure.
Figure 5:
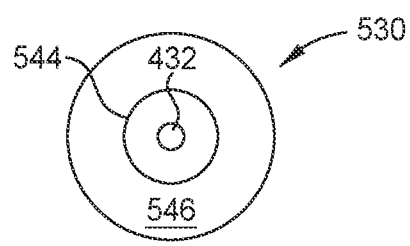
FIG. 5 illustrates an example front view of an optical fiber with a core, an inner cladding, and an outer cladding, according to some embodiments of the present disclosure.

FIGS. 4 and 5 illustrate two different types of optical fibers that may be used for illumination within probe 304. FIG. 4 illustrates an optical fiber 430 including a core 432 as well as a cladding 434. In certain embodiments, core 432 comprises fused silica, glass, or similar material. Light source 108 is configured to focus an illumination light (e.g., white light-emitting diode (LED) light) onto the proximal end of core 432 and/or cladding 434, such that the illumination light is propagated along an entire length of core 432 and/or cladding 434.

In certain embodiments, cladding 434 may comprise fused silica, glass, or similar material. Cladding 434 is doped with one or more dopants such as fluorine, chlorine, boron, or any combination of the above, according to some embodiments. The dopants reduce the refractive index of the cladding 434. Cladding 434, as doped, has a lower refractive index than core 432, thereby creating light guiding properties within core 432. When an optical fiber having a core and a single layer of cladding (referred to sometimes as a single-cladded fiber), such as optical fiber 430 is used, the cladding (referred to as cladding 434 here) is removed where openings, such as openings 320, are located (or where openings 320 interface with optical fiber 430) on probe 304 to allow core 432 to emit light from the openings. For example, similar to how openings 320 are created in probe 304, pieces with the same size as of openings 320 may be stripped from cladding 434 to expose core 432. In another example, larger portions of cladding 434 may be removed. Note that although fiber 430 includes a cladding 434, in some embodiments, optical fiber 430 may not include cladding 434. In such embodiments, optical fiber 430 only includes core 432.

FIG. 5 illustrates an optical fiber 530 including a core 432, an inner cladding 544, as well as an outer cladding 546.

Inner cladding 544 is similar to cladding 434 but it is thinner; although that does not always have to be the case. Outer cladding 546, in some embodiments, comprises fused silica, glass or some other material. In certain embodiments, described in relation to FIG. 6, light source 108 is configured to focus a first illumination light from a first illumination light source onto the proximal end of core 432, such that the first illumination light is propagated along an entire length of core 432, and also focus a second illumination light from a second illumination light source onto the proximal end of outer cladding 546, such that the second illumination light is propagated along an entire length of outer cladding 546. In such embodiments, outer cladding 546 itself is able to emit light, meaning that outer cladding 546 propagates light through openings 320 and therefore does not need to be removed or stripped. In certain embodiments, light source 108 may be configured to focus a laser beam onto the proximal end of core 432 and focus an illumination light onto the proximal end of outer cladding 546 and/or core 432. The laser beam may be a surgical treatment beam used for photocoagulation.

In certain embodiments, outer cladding 546 is not used for emitting light, in which case both outer cladding 546 and inner cladding 544 are stripped where openings 320 are located to allow for core 432 to propagate light through openings 320.

Figure 6:
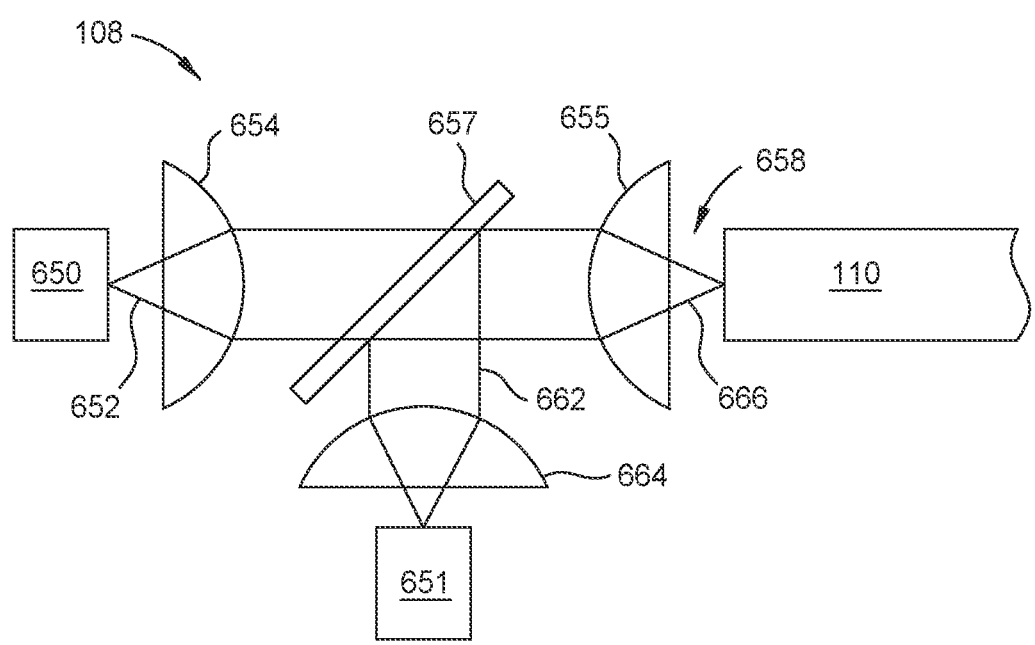
FIG. 6 illustrates an example plan view of a light source, in accordance with a particular embodiment of the present disclosure.

FIG. 6 illustrates an example plan view of light source 108, in accordance with a particular embodiment of the present disclosure. As shown, light source 108 includes a first lens 654 (e.g., collimating lens), a beam splitter 657, a fiber optic cable 110, a second lens 655 (e.g., focusing lens), a third lens 664 (e.g., collimating lens), a first illumination light source 650, and a second illumination light source 651. The beam splitter 657, which may be a dichroic beam splitter, is downstream from the first lens 654, the second lens 655 is downstream from the beam splitter 657, and the fiber optic cable 110, including an optical fiber such optical fiber 530, is downstream from the second lens 655.

The illumination light source 650 emits an illumination light 652, referred to as the first illumination light. The illumination light 652 can be any spectrum of light, including, but not limited to, visible light or white light. The illumination light source 650 can be a light-emitting diode (LED) or a broadband laser source. The illumination light 652 is collimated by the first lens 654 such that the illumination light 652 is transformed into a beam of light with parallel rays, as shown. The first lens 654 can be any lens, including a plano-convex, or biconvex lens, etc. The beam splitter 657 does not affect or has limited effect on the illumination light 652, and thus the illumination light 652 passes through the beam splitter 657. The illumination light 652 is then focused by the second lens 655, as shown. The second lens 655 can be any lens used to focus light, including a plano-convex or biconvex lens. The illumination light 652 is focused and incident on the fiber optic cable 110.

Illumination light source 651 emits an illumination light 662, referred to as the second illumination light. The illumination light 662 is collimated by the third lens 664 such that the illumination light 662 is transformed into a beam of light with parallel rays, as shown. The third lens 664 can be any lens, including a plano-convex, biconvex lens. Illumination light 662 may have a different wavelength than illumination light 652, causing beam splitter 657 to reflect illumination light 662 instead of allowing it to pass through. For example, illumination light 662 may be a green beam.

In some embodiments, the fiber optic cable 110 is coupled to the light source 108 through a port adaptor. The port adaptor includes a ferrule with an opening that allows illumination light 652 and illumination light 662, as described below, from light source 108 to be propagated into an interface plane (also referred to as a proximal entrance plane) of the proximal end of optical fiber 530 inside fiber optic cable 110. In other words, the proximal end of the ferrule exposes the interface plane of the proximal end of optical fiber 530. As described above, second lens 655 is configured to focus a combination of illumination lights 652 and 662, also referred to as multiplexed light 666, onto the proximal end optical fiber 530. More specifically, second lens 655 is configured to focus illumination light 652 onto the proximal end of core 432 and illumination light 662 into the proximal end of outer cladding 546, or vice versa. In such an example, illumination light 652 is propagated through core 432 from the distal end 324 of probe 304 while is propagated through outer cladding 546 through openings 320.

In the example of FIG. 6, because two different and independent illumination light sources are used, a user may turn each of the illumination lights off and on independently. For example, illumination light 652, which is propagated from the distal end 324 of probe 304 may remain on throughout the duration of the surgery while illumination light 662, which is propagated from openings 320, may be turned on and off as needed. Turning these lights on and off may be performed using one or more switches on the handpiece 102, or some other user interface (e.g., a user interface provided by a console coupled to the handpiece 102).

In some embodiments, second lens 655 may be configured to focus illumination light 652 onto the proximal end of core 432 and illumination light 662 into the proximal end of core 432, inner cladding 544, and outer cladding 546, or vice versa. In some embodiments, second lens 655 may be configured to focus both illumination lights 652 and 662 onto the proximal end of core 432, inner cladding 544, and outer cladding 546. In embodiments where optical fiber 430 is used, light source 108 may comprise only a single illumination light source, such as illumination light source 651, which may focus an illumination light on core 432 and/or cladding 434

Figure 7:
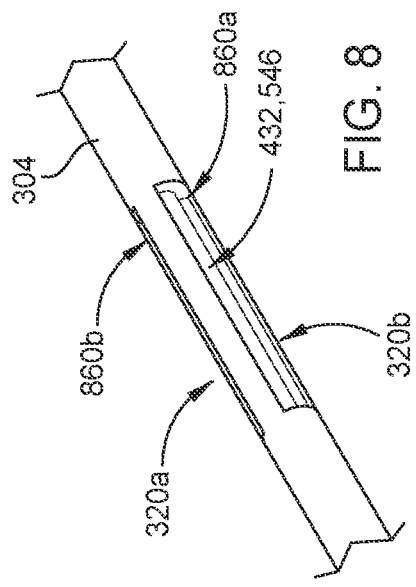
FIG. 7 illustrates a perspective view of the probe of FIG. 3, according to some embodiments of the present disclosure.

FIG. 7 illustrates a perspective view of probe 304 of FIG. 3, including openings 320a and 320b. FIG. 7 also illustrates an outer layer of a fiber through opening 320a. The outer layer may be core 432 of fiber 430 or outer cladding 546 of fiber 530.

Figure 8:
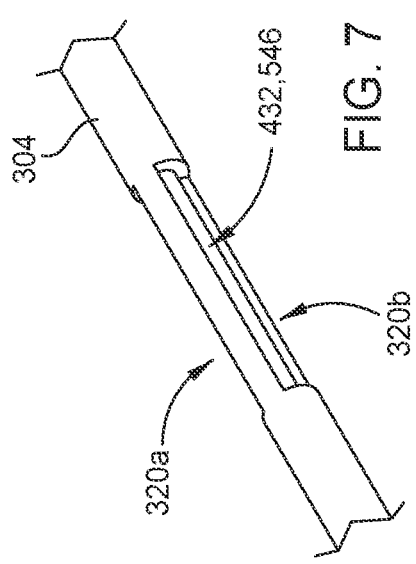
FIG. 8 illustrates a perspective view of the probe of FIG. 3 with transparent elements, according to some embodiments of the present disclosure.

FIG. 8 illustrates a perspective view of probe 304 of FIG. 3, including openings 320a and 320b, as well as transparent elements 860. Transparent elements 860 are placed in openings 320 (e.g., in place of the pieces of probe 304 that were removed to provide openings 320) and, therefore, have some of the same dimensions as openings 320. Transparent elements 860 are shaped such that the inner surfaces of the transparent elements 860 interface with the outer surfaces of the fiber (e.g., outer surfaces of the cladding) inside the probe 304. Transparent elements 860 may comprise any transparent material, such as transparent plastic, glass, etc. More specifically, some example materials may include polycarbonate (PC), polypropylene (PP), polytetrafluoroethylene (PTFE), polyvinylchloride (PVC), polyetherimide ("ultem," PEI). Transparent elements 860 are configured to allow illumination light to pass through while also providing support to probe 304 to help maintain the structural integrity of probe 304. In other words, transparent elements 860 help stiffen or strengthen the part of probe 304, where openings 320 are located, that might otherwise not be stiff enough.

Transparent elements 860 may be machined and adhered to the inner surface of probe 304. In addition, each of the transparent elements 860 may be configured with a size larger than (e.g., slightly larger) the size of a corresponding opening 320, such as to prevent the transparent element 860 from becoming loose or separating from probe 304. In one example, a transparent element that is larger in size than a corresponding opening is press fitted into the opening.

Figure 9A:
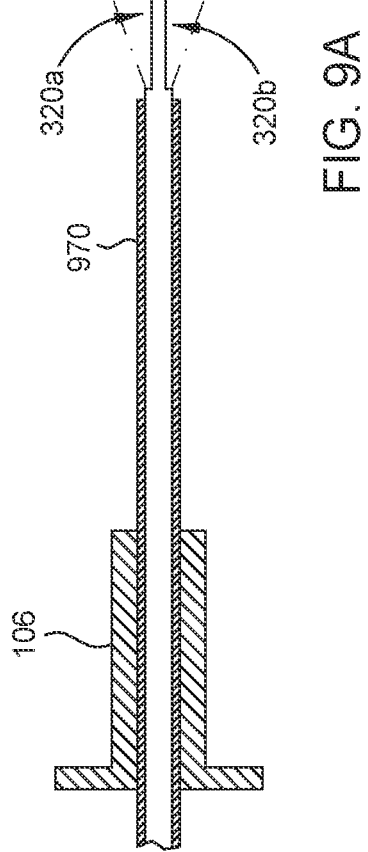

FIG. 9A illustrates an example sleeve or outer tube 970 that surrounds probe 304. As shown, outer tube 970 is configured to be inserted into the eye through the insertion cannula 106. The proximal end of outer tube 970 is configured to be directly or indirectly coupled to a handpiece (e.g., handpiece 102 of FIG. 1). In the example of FIGS. 9A-9C, outer tube 970 is stationary while probe 304 may be retracted or protracted by the handpiece and with respect to outer tube 970. A hand-activated or automated mechanism provided by the handpiece may be used to protract and retract probe 304. One of a variety of mechanisms may be used for retracting and protracting probe 304. One example of such a mechanism may be provided by an Articulating Illumination Laser Prove handpiece sold by Alcon Vision, LLC of Fort Worth, Tex. In the example of FIG. 9A, outer tube 970 does not cover openings 320, leaving them exposed. In this state, probe 304 may be referred to as being in a wide-angle state. However, retracting probe 304 towards insertion cannula 106 causes the outer tube 970 to cover openings 320, thereby, blocking any light that may be propagated through openings 320. In this state, probe 304 may be referred to as being in a narrow-angle state.

In another example, outer tube 970 may be protracted and retracted while probe 304 is stationary. One of a variety of hand-activated or automated mechanisms may be used for retracting and protracting outer tube 970.

Using a mechanism, such as one of the mechanisms described above, a surgeon is able to turn the light that is propagated through openings 320 off and on by covering and uncovering openings 320 with outer tube 970. Also, in some embodiments, outer tube 970 is stiffer than probe 304. In such embodiments, the surgeon may first insert the outer tube 970 into the eye, while probe 304 does not extend beyond outer tube 970. Then the surgeon may protract probe 304, thereby, uncovering openings 320.

FIG. 9B illustrates an example perspective view of outer tube 970 covering openings 320.

FIG. 9C illustrates an example perspective view of probe 304 where openings 320 are not covered by outer tube 970.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims. Those skilled in the art will appreciate that the light source, the endoilluminators, and the tube illustrated in the figures can include more components than the simplified illustrations described herein. The endoilluminators described herein include only those components useful for describing some prominent features of implementations within the scope of the claims. Also, note that although some of the embodiments herein are described in relation to ophthalmic surgery, the scope of the disclosure is not limited to ophthalmic surgery. For example, the embodiments described herein may be implemented in endoilluminators used for illuminating other body parts during other types of surgery.

What is claimed is:

1. An endoilluminator, comprising:
a probe housing an optical fiber, wherein:
the probe comprises a distal end with an opening, through which a first light from a distal end of the optical fiber is configured to be propagated; and
the probe comprises one or more side openings through which a second light from one or more sides of the optical fiber is configured to be propagated; and
a handpiece coupled to a light source and a proximal end of the probe, wherein the light source is configured to drive light into the optical fiber;
the handpiece comprises an outer tube that surrounds the probe;
the outer tube is fixedly coupled to the handpiece;
the probe is configured to be retracted and protracted with respect to the outer tube;
when the probe is in a wide-angle state, retracting the probe with respect to the outer tube causes the outer tube to cover the side openings; and
when the probe is in a narrow-angle state; protracting the probe with respect to the outer tube causes an exposure of the side openings.

2. The endoilluminator of claim 1, wherein the one or more side openings comprise two rectangular slots on two sides of the probe.

3. The endoilluminator of claim 1, wherein:
the optical fiber comprises a core and a cladding;
the cladding is stripped where the one or more side openings interface with the optical fiber; and
the first light and the second light are propagated by the core.

4. The endoilluminator of claim 1, wherein:
the optical fiber comprises a core, an inner cladding, and an outer cladding;
the core propagates the first light; and
the outer cladding propagates the second light.

5. An endoilluminator, comprising:
a probe housing an optical fiber, wherein:
the probe comprises a distal end with an opening through which a first light from a distal end of the optical fiber is configured to be propagated; and
the probe comprises one or more side openings through which a second light from one or more sides of the optical fiber is configured to be propagated; and
a handpiece coupled to a light source and a proximal end of the probe, wherein the light source is configured to drive light into the optical fiber;
the handpiece comprises an outer tube that surrounds the probe;
the probe is coupled to the handpiece;
the outer tube is configured to be retracted and protracted with respect to the probe;
when the probe is in a wide-angle state, protracting the outer tube with respect to the probe causes the outer tube to cover the side openings; and
when the probe is in a narrow-angle state, retracting the outer tube with respect to the probe causes an exposure of the side openings.

6. The endoilluminator of claim 5, wherein the one or more side openings comprise two rectangular slots on two sides of the probe.

7. The endoilluminator of claim 5, wherein:
the optical fiber comprises a core and a cladding;
the cladding is stripped where the one or more side openings interface with the optical fiber; and the first light and the second light are propagated by the core.

8. The endoilluminator of claim 5, wherein:
the optical fiber comprises a core, an inner cladding, and an outer cladding;
the core propagates the first light; and
the outer cladding propagates the second light.

9. An endoilluminator, comprising:
a probe housing an optical fiber, wherein:
 the probe comprises a distal end with an opening through which a first light from a distal end of the optical fiber is configured to be propagated; and
 the probe comprises one or more side openings through which a second light from one or more sides of the optical fiber is configured to be propagated; and
a handpiece coupled to a light source and a proximal end of the probe, wherein the light source is configured to drive light into the optical fiber;
wherein one or more transparent elements are placed in the one or more side openings.

10. The endoilluminator of claim 9; wherein the one or more transparent elements are shaped such that inner surfaces of the one or more transparent elements interface with outer surfaces of the optical fiber.

11. The endoilluminator of claim 9, wherein the one or more transparent elements comprise one of polycarbonate (PC), polypropylene (PP), polytetrafluoroethylene (PTFE), polyvinylchloride (PVC), or polyetherimide.

12. The endoilluminator of claim 9, wherein a size of each of the one or more transparent elements is larger than a size of a corresponding side opening of the one or more side openings.

13. The endoilluminator of claim 9, wherein the one or more side openings comprise two rectangular slots on two sides of the probe.

14. The endoilluminator of claim 9, wherein:
the optical fiber comprises a core and a cladding;
the cladding is stripped where the one or more side openings interface with the optical fiber; and
the first light and the second light are propagated by the core.

15. The endoilluminator of claim 9, wherein:
the optical fiber comprises a core, an inner cladding, and an outer cladding;
the core propagates the first light; and
the outer cladding propagates the second light.

* * * * *